United States Patent
Lee et al.

(10) Patent No.: US 10,532,968 B2
(45) Date of Patent: Jan. 14, 2020

(54) METHOD FOR PURIFYING PHENOL

(71) Applicant: LG CHEM, LTD., Seoul (KR)

(72) Inventors: Si Nae Lee, Daejeon (KR); Sung Kyu Lee, Daejeon (KR); Joon Ho Shin, Daejeon (KR)

(73) Assignee: LG CHEM, LTD., Seoul (KR)

( * ) Notice: Subject to any disclaimer, the term of this patent is extended or adjusted under 35 U.S.C. 154(b) by 0 days.

(21) Appl. No.: 16/071,553

(22) PCT Filed: Nov. 10, 2017

(86) PCT No.: PCT/KR2017/012740
§ 371 (c)(1),
(2) Date: Jul. 20, 2018

(87) PCT Pub. No.: WO2018/088846
PCT Pub. Date: May 17, 2018

(65) Prior Publication Data
US 2019/0023634 A1    Jan. 24, 2019

(30) Foreign Application Priority Data
Nov. 9, 2017 (KR) .................. 10-2017-0148530

(51) Int. Cl.
| | | |
|---|---|---|
| C07C 37/78 | (2006.01) | |
| C07C 39/04 | (2006.01) | |
| B01D 3/32 | (2006.01) | |
| B01D 3/36 | (2006.01) | |
| C07C 45/84 | (2006.01) | |

(52) U.S. Cl.
CPC ............... *C07C 37/78* (2013.01); *B01D 3/32* (2013.01); *B01D 3/36* (2013.01); *C07C 39/04* (2013.01); *C07C 45/84* (2013.01); *B01D 2257/70* (2013.01)

(58) Field of Classification Search
CPC ........ B01D 3/36; B01D 3/32; B01D 2257/70; C07C 45/84; C07C 37/78
See application file for complete search history.

(56) References Cited

U.S. PATENT DOCUMENTS

| | | | |
|---|---|---|---|
| 3,405,038 A * | 10/1968 | Kohmoto | ................ C07C 37/74 |
| | | | 203/69 |
| 5,254,751 A | 10/1993 | Zakoshansky | |
| 6,555,719 B2 * | 4/2003 | Sigg | ....................... C07C 37/08 |
| | | | 568/716 |
| 9,242,909 B2 | 1/2016 | Takeshita et al. | |
| 9,783,469 B2 | 10/2017 | Takeshita et al. | |

(Continued)

FOREIGN PATENT DOCUMENTS

| | | | |
|---|---|---|---|
| JP | 47-14969 B2 | 5/1972 | |
| JP | 6-293682 A | 10/1994 | |

(Continued)

*Primary Examiner* — Rosalynd A Keys
(74) *Attorney, Agent, or Firm* — Dentons US LLP (57) ABSTRACT

The present invention relates to a method for purifying phenol, which comprises: supplying a feed comprising phenol, acetone, hydroxyacetone and water to a distillation column at 60° C. to 95° C.; separating the feed into a first fraction, which comprises the acetone, and separates to the upper part of the distillation column and a second fraction, which comprises the phenol, and separates to the lower part of the distillation column; and recovering the first fraction and the second fraction, respectively.

6 Claims, 2 Drawing Sheets

(56) References Cited

U.S. PATENT DOCUMENTS

| | | | |
|---|---|---|---|
| 9,895,625 B2 | 2/2018 | Lee et al. | |
| 2002/0068840 A1 * | 6/2002 | Weber | C07C 37/74 |
| | | | 568/385 |
| 2011/0272268 A1 | 11/2011 | Takeshita et al. | |
| 2015/0083578 A1 | 3/2015 | Lee et al. | |
| 2016/0090339 A1 | 3/2016 | Takeshita et al. | |

FOREIGN PATENT DOCUMENTS

| | | | | |
|---|---|---|---|---|
| JP | 2015-524818 A | 8/2015 | | |
| JP | 2015-178475 A | 10/2015 | | |
| JP | 2016-060708 A | 4/2016 | | |
| KR | 10-2006-0026476 A | 3/2006 | | |
| KR | 10-2006-0130209 A | 12/2006 | | |
| KR | 10-2008--109765 A | 12/2008 | | |
| KR | 10-2011-0134075 A | 12/2011 | | |
| WO | WO-2005005357 A1 * | 1/2005 | | B01D 3/007 |
| WO | 2009/123223 A1 | 10/2009 | | |
| WO | 2010/073841 A1 | 7/2010 | | |

\* cited by examiner

METHOD FOR PURIFYING PHENOL

CROSS-REFERENCE TO RELATED APPLICATION

This application is a National Stage filing under 35 U.S.C. 371 of International Application No. PCT/KR2017/012740 filed on Nov. 10, 2017, and claims priority to and the benefit of Korean Patent Application No. 10-2016-0151394 filed on Nov. 14, 2016, and Korean Patent Application No. 10-2017-0148530 filed on Nov. 9, 2017, the disclosures of which are incorporated herein by reference in their entirety.

TECHNICAL FIELD

Background Art

Phenol is prepared by a process including oxidation of an alkylaryl compound into an alkylaryl hydroperoxide, concentration of the alkylaryl hydroperoxide, cleavage of the concentrate into phenol and ketone using an acid catalyst, neutralization of the acid-cleavage product, and fractional distillation of the neutralized cleavage product.

For example, as a method for preparing phenol, a method for preparing phenol by acid decomposing cumene hydroperoxide obtained by oxidation is known. In this method, the acid decomposition product contains phenol and acetone as main components, and also contains all types of byproducts including α-methyl styrene, acetophenone, 4-cumylphenol, 2-phenyl-2-propanol and unreacted cumene, and all types of carbonyl compounds including a very small amount of hydroxyacetone (HA) and α-phenylpropionaldehyde (α-PPA). However, while a polycarbonate is prepared with bisphenol-A, which is a phenol derivative, there is a demand for high purity phenol in polycarbonate applications.

To obtain such high purity phenol, a phenol fraction in which most of a low-boiling-point material such as acetone, cumene, water, or α-methyl styrene and a high-boiling-point material such as acetophenone or 2-phenyl-2-propanol are removed from a neutralized product of the acid decomposition product by distillation is further purified to remove an aliphatic carbonyl compound such as hydroxyacetone and an aromatic carbonyl compound such as α-phenylpropionaldehyde, but it is particularly difficult to remove these carbonyl compounds from phenol, and therefore the quality of the final product, phenol, is degraded. Accordingly, it is important to remove carbonyl compounds as much as possible by a fractional distillation process.

Meanwhile, in high purity phenol, it is important to remove hydroxyacetone (HA), among various impurities. The hydroxyacetone acts as a key factor for determining the quality of phenol in addition to a material such as 2-methylbenzofuran or mesityl oxide, and particularly, unless most of the hydroxyacetone is removed from a first column of a purification process, purification efficiency is extremely degraded in an ion exchange resin generally equipped in a subsequent purification process, resulting in the degradation in quality of the final product.

For this reason, to separate the hydroxyacetone, various attempts have been made to install a plurality of columns or a reactor, but they have problems of excessive installation and equipment expenses, and thus, the initial expenses or operating expenses for factory facilities lead to low competitiveness. In addition, there was an attempt to separately apply a method for separating hydroxyacetone, cumene, or α-methyl styrene by additionally installing an extraction stream at the middle part of a column. However, since cumene is an ingredient for producing phenol and acetone, and α-methyl styrene can be commercially available and converted into cumene by performing an additional reaction after recovery, unless a post-treatment process is performed after the cumene and α-methyl styrene separate into the middle part, operating costs are rather increased, which does not help in the achievement of competitiveness in a processing operation.

In addition, in the case of the column for removing hydroxyacetone from the middle part, since all of the concentrations of hydroxyacetone at the upper and lower parts should be considered, it may be further difficult to operate the column. If the column is in an unstable state, hydroxyacetone may not be removed from the middle part, but may be present in all of the upper and lower parts. Therefore, a subsequent process can be an adversely affected.

DISCLOSURE

Technical Problem

The present invention is directed to providing a method for purifying phenol by controlling the temperature of a feed comprising phenol, acetone, hydroxyacetone and water, which are input into a distillation column in a fractional distillation process, to reduce a content of hydroxyacetone in the fraction comprising the phenol, which is subjected to the distillation process.

Technical Solution

To solve the above object, the present invention provides a method for purifying phenol, which comprises: supplying a feed comprising phenol, acetone, hydroxyacetone and water to a distillation column at 60 to 95° C.; separating the feed into a first fraction which comprises the acetone and separates into the upper part of the distillation column and a second fraction which comprises the phenol and separates into the lower part of the distillation column; and recovering the first fraction and the second fraction, respectively.

Advantageous Effects

According to the method for purifying phenol of the present invention, as the temperature of a feed provided to a distillation column is controlled, the separation efficiency of hydroxyacetone can be improved, and the hydroxyacetone can separate into the upper part while minimizing the diffusion thereof to the lower part. Therefore, a content of the hydroxyacetone in the fraction comprising phenol can be considerably reduced.

MODES OF THE INVENTION

Hereinafter, to help in understanding the present invention, the present invention will be described in further detail.

The terms and words used herein and in the claims should not be interpreted as being limited to conventional or literal meanings, but should be interpreted with meanings and concepts which are consistent with the technological scope of the invention based on the principle that the inventors have appropriately defined concepts of terms in order to describe the invention in the best way.

A purification apparatus used in a method for purifying phenol according to an exemplary embodiment of the present invention may be any apparatus used in the art of the present invention without particular limitation, but for better understanding, an example will be described with reference to FIG. 1.

Figure 1:
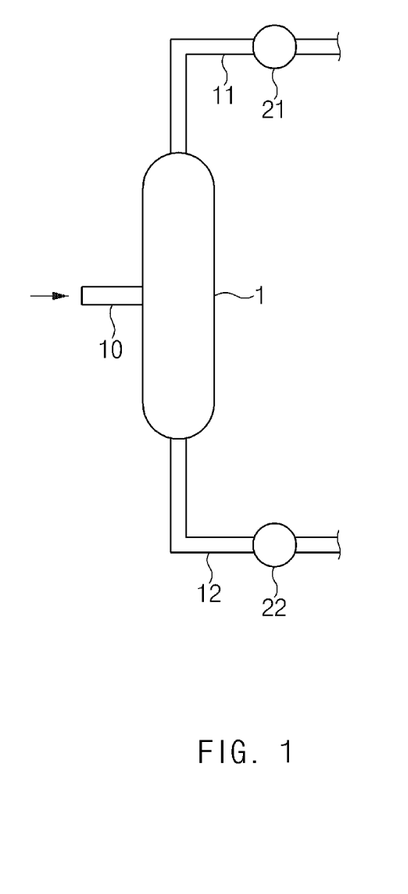
FIG. 1 shows an example of a purification apparatus used in the present invention.

Referring to FIG. 1, the purification apparatus used in the method for purifying phenol of the present invention comprises a distillation column 1, a middle inlet 10 located at the side of the distillation column 1, a first line 11 connected with the upper part of the distillation column 1 and a second line 12 connected with the lower part of the distillation column 1.

The distillation column 1 refers to a section in which fractional distillation is performed to separate phenol from a feed comprising phenol, acetone, hydroxyacetone and water. The distillation column used in the present invention may be a distillation tower.

The middle inlet 10 refers to an opening for supplying the feed.

The first line 11 refers to a line through which a first fraction comprising acetone, specifically, acetone vapor, separated by performing fractional distillation in the distillation column 1 is recovered, and may be connected with an acetone purification column (not shown) for additional purification of the acetone. A switch may be located between the distillation column 1 and the first line 11, and a reflux condenser 21 for the first fraction may be installed at the first line 11.

The second line 12 refers to a line through which a second fraction comprising phenol separated by performing fractional distillation in the distillation column 1, and may be connected with a phenol purification column (not shown) for additional purification of the phenol. A switch may be located between the distillation column 1 and the second line 12, and a heat exchanger 22 for introducing suitable heat energy to the distillation column 1 may be installed at the second line 12.

The distillation column 1 may further comprise a reflux pump (not shown). A part or all of the first fraction recovered at the upper part of the distillation column 1 using the reflux pump may be input again to the upper part through a third line (not shown) and further purified with the first fraction previously present in the upper part of the distillation column 1.

In addition, the purification apparatus may have outlets only at the upper and lower parts, and a stream extracted to the middle part may not be present. In the phenol purification process, a line for extracting phenol and acetone fractions at the middle part of the separation column is installed to necessarily insert streams for separating an unreacted phenol precursor (e.g., cumene), hydroxyacetone and α-methyl styrene, or one or more columns for removing hydroxyacetone from a phenol fraction separated from the lower part are necessarily present in general.

However, when the purification apparatus used in the method for purifying phenol according to one exemplary embodiment of the present invention is used, and the temperature of the provided feed is suitably controlled, it is not necessary to have a separate separation stream as described above, and therefore the efficiency of the purification process may be maximized, and the efficiency of removing impurities such as hydroxyacetone may also be maintained at the same or higher level as the process efficiency. In addition, separate columns that are necessarily present to remove hydroxyacetone and 2-methylbenzofuran may not be needed. For this reason, the process can be simplified, and efficiency can be increased.

The method for purifying phenol according to an exemplary embodiment of the present invention may comprise supplying a feed comprising phenol, acetone, hydroxyacetone and water to the distillation column 1 at 60 to 95° C.

The feed may be prepared by oxidizing an alkylaryl compound to prepare a reaction mixture comprising an alkylaryl hydroperoxide and an unreacted alkylaryl compound, and performing a cleavage reaction on the reaction mixture. Specifically, the feed may be a cleave product mixture comprising phenol, acetone, hydroxyacetone and water, which is produced by oxidizing cumene to prepare cumene hydroperoxide, and performing a cleavage reaction on a reaction mixture comprising the cumene hydroperoxide and unreacted cumene to in the presence of an acid catalyst.

Meanwhile, the oxidation of the cumene may be generally carried out by automated oxidation using an oxygen-containing gas such as air or oxygen-concentrated air. In addition, the oxidation may be performed using an additive such as an alkali, or without an additive. The additive may be an alkali metal compound such as sodium hydroxide (NaOH) or potassium hydroxide (KOH), an alkali earth metal compound, an alkali metal carbonate such as sodium carbonate ($Na_2CO_3$) or sodium bicarbonate ($NaHCO_3$), ammonia, or ammonium carbonate. In addition, the oxidation may be performed at approximately 50 to 200° C. and under an atmospheric pressure to approximately 5 MPa.

The oxidation of cumene may be carried out using multiple oxidation reactors which are used in a conventional phenol process, specifically, three oxidation reactors. A cumene hydroperoxide-containing stream prepared by oxidizing a stream containing 80% or more, specifically 99 wt % or more cumene in the presence of an oxygen-containing stream may be used. To promote cumene oxidation, a conventional initiator may be used. The initiator may be an organic hydroperoxide such as cumene hydroperoxide or t-butyl hydroperoxide, a peroxy-based free radical initiator, or an azo-based free radical initiator.

The reaction mixture comprising the cumene hydroperoxide and unreacted cumene may comprise 60 to 95 wt % of the cumene hydroperoxide with respect to the total weight of the reaction mixture. The acid catalyst used in the cleavage reaction may be an inorganic acid, an organic acid, an acidic ion exchange resin and a solid acid. The inorganic acid includes sulfonic acid ($H_2SO_4$), sulfur dioxide ($SO_2$), etc., and the organic acid includes toluenesulfonic acid or benzenesulfonic acid. The acidic ion exchange resin includes a sulfonated styrene-divinylbenzene resin, etc., and the solid acid includes a zeolite, alumina, etc.

The method for purifying phenol according to the present invention may be included in the method for preparing phenol as described above, and a different method, other than the above-described method for preparing phenol, may be applied, but the method for preparing phenol is not limited thereto.

The feed may comprise the phenol at 40 to 70 wt %, the acetone at 15 to 45 wt %, the hydroxyacetone at 0.02 to 5 wt %, and the water at 9 to 11 wt % with respect to the total weight of the feed.

The water should be included in the feed within the above-mentioned range, but may reduce a content of the hydroxyacetone in a second fraction that will be described below. In addition, due to the water, an amount of phenol separated into a first fraction that will be described below may not only be minimized, but an amount of α-methyl styrene separated into a second fraction that will be described below may also be minimized. As a result, the loss of phenol and α-methyl styrene may be minimized. When the above-mentioned content range is not satisfied, the reflux of the hydroxyacetone may not be suitably performed in the fractional distillation process, a large amount of the hydroxyacetone may remain in the second fraction that will be described below without suitably moving to a first fraction that will be described below.

The feed may further comprise a byproduct, which may be produced in the above-mentioned oxidation and cleavage processes, and the byproduct may be, for example, one or two or more selected from the group consisting of cumene, α-methyl styrene, methanol, acetaldehyde, formaldehyde, cumylphenol, dicumyl peroxide, an α-methyl styrene dimer, mesityl oxide, 2-methylbenzofuran and phenol tar.

The feed may be provided to the distillation column 1 through the middle inlet 10 at 60 to 95° C., specifically, 75 to 95° C., and more specifically, 80 to 95° C. Here, a pressure may be 2 atm or less.

In the purification process, when a temperature of the feed to be provided to the distillation column is high, a material of the provided feed, which should separate into the lower part, moves to the upper part, the efficiency of refluxing the material in the upper part is degraded, resulting in degraded purity of a product. By comparison, energy efficiency is considerably increased, and therefore the feed is generally provided by being heated until an optimal temperature range.

For this reason, also in the phenol purification process, purification was performed by heating the feed in the first distillation column in a suitable temperature range of 100° C. or more. However, in this case, since a considerably large amount of hydroxyacetone is contained in a phenol fraction due to low efficiency of separating the hydroxyacetone, it is necessary to have an additional column, or a column for separating the feed to a middle part, rather than the upper and lower parts.

However, according to the method for purifying phenol according to an exemplary embodiment of the present invention, by controlling the feed temperature range within 60 to 95° C. as described above, hydroxyacetone separation efficiency may be improved, and a critical temperature for supplying the feed, at which hydroxyacetone separates into the upper part without separating into the lower part, is determined.

When the feed supply temperature is less than 60° C., since the amount of hydroxyacetone removed is very small, compared to energy provided to the distillation column 1, that is, energy consumed in a reboiler of the distillation column 1, process efficiency may be even reduced. In addition, since the effect of reducing hydroxyacetone is exhibited at the equivalent level to when the feed supply temperature is 60 to 95° C., but energy consumed in a reboiler of the distillation column is increased, this is not preferable in terms of energy efficiency.

In addition, when the feed supply temperature exceeds 95° C., the energy consumed in the reboiler of the distillation column 1 is reduced, but the amount of the hydroxyacetone input to the lower part is rapidly increased, and therefore, there is a possibility that a separate separation column is needed, which is similar to the conventional method for purifying phenol.

To satisfy the above-mentioned temperature range, the feed may be performed a cleavage process in the process of preparing phenol, cooling to 50° C. or less, and a separate heating process. In addition, the feed may be supplied to the distillation column after the cleavage process, and then cooling only to the above-mentioned temperature range.

Meanwhile, when the feed is a mixture of cleaved products, since it was performed cleavage reaction using an acid catalyst, it may have a too low pH for the second step to be effectively carried out. For this reason, to suitably carry out the second step, that is, to prevent a purification apparatus such as the distillation column 1 from being strained, such as the corrosion of a purification apparatus, the feed may be supplied to the distillation column by controlling the pH to be 3 to 10, specifically 4 to 7, using a base. The base may be a sodium hydroxide solution, NaOH, ammonia, ammonium hydroxide, amine or diamine.

The method for purifying phenol according to an exemplary embodiment of the present invention may comprise separating the feed into a first fraction which comprises the acetone and separates to the upper part of the distillation column 1 and a second fraction which comprises the phenol and separates to the lower part of the distillation column.

To separate the feed into the first and second fractions, distillation may be performed one or twice or more.

The first fraction refers to a fraction comprising the acetone as a main component, and the second fraction refers to a fraction comprising the phenol as a main component. The second fraction may obtain a phenol fraction which comprises hydroxyacetone only at 0.02 wt % or less, that is, 200 ppm or less with respect to the total weight of the second fraction through the second step, that is, distillation which satisfies the temperature range for the suggested feed as described above.

Meanwhile, a temperature of the upper part of the distillation column 1 may be lower than the lower part of the distillation column 1 during the second step. Specifically, a temperature of the upper part of the distillation column 1 may be 65 to 115° C., specifically, 78 to 115° C. A temperature of the lower part of the distillation column 1 may be 170 to 225° C., specifically, 193 to 216° C. An inner pressure of the distillation column 1, that is, an operating pressure may be 0 to 1 kgf/cm$^2$·g. When the above-mentioned temperature and pressure conditions are satisfied, the reflux of the feed in the distillation column may effectively occur to easily perform separation of the feed into the first and second fractions.

However, the operating pressure or the feed composition may have a low relevance with the separation efficiency of hydroxyacetone, and may be the conditions that are optimized for the separation efficiency in the whole purification process, and when the operating pressure or the feed composition satisfies the above-mentioned ranges, the above-mentioned effect of maximizing the separation efficiency of the hydroxyacetone may be achieved.

Here, the upper part of the distillation column 1 refers to the upper end of the distillation column 1, not generically referring to a region of the distillation column 1 in which a first fraction is located. The lower part of the distillation column 1 refers to the lower end of the distillation column, not generically referring to a region of the distillation column 2 in which a second fraction is located.

The method for purifying phenol according to an exemplary embodiment of the present invention may comprise recovering the first fraction and the second fraction, respectively.

The first fraction may be recovered through a first line 11 connected to the upper part of the distillation column 1. The second fraction may be recovered through a second line 12 connected to the lower part of the distillation column 1. The first fraction may be transferred to an acetone purification column (not shown) through the first line 11, and the second fraction may be transferred to a phenol purification column (not shown) through the second line 12.

The method for purifying phenol according to an exemplary embodiment of the present invention may comprise a post-treatment process to remove hydroxyacetone and a byproduct that may be present in the second fraction, specifically, 2-methylbenzofuran and mesityl oxide. The post-treatment process may allow the hydroxyacetone, 2-methylbenzofuran and mesityl oxide to be converted into a high-boiling-point material by reacting the second fraction in an ion exchange resin-charged reactor.

However, in the method for purifying phenol according to an exemplary embodiment of the present invention, most of the hydroxyacetone is removed by applying a control condition, such as the control of a suitable temperature in a distillation column of the purification process, to the line through which the hydroxyacetone is added in the post-treatment process when the post-treatment process is performed, and therefore, the efficiency of removing a material such as 2-methylbenzofuran or mesityl oxide using an ion exchange resin may be highly improved.

The post-treatment process continuously uses a plurality of reactors comprising the ion exchange resin, and the hydroxyacetone, 2-methylbenzofuran and mesityl oxide in the second fraction may be effectively removed without distillation which consumes energy between two reactors comprising the ion exchange resin by setting a temperature of the reactor to, specifically, 65 to 95° C., and more specifically, 70 to 90° C. This is because, when the second fraction is in contact with the ion exchange resin, hydroxyacetone and 2-methylbenzofuran may react with the ion exchange resin, thereby being converted into a high-boiling-point material. In addition, the mesityl oxide may react with the phenol, thereby being converted into a high-boiling-point material and water. In addition, in the presence of water formed by a reaction between the hydroxyacetone and the phenol, a part of the mesityl oxide may be degraded to acetone in the ion exchange resin. The acetone may further react with the phenol to become bisphenol A. The post-treatment process may facilitate the conversion of undesired byproducts, such as hydroxyacetone, 2-methylbenzofuran and mesityl oxide, in the second fraction into high-boiling point materials which can be easily removed from phenol purified in the final distillation step after the second fraction is in contact with the ion exchange resin.

Meanwhile, the ion exchange resin may refer to a hydrogen-type cation exchange resin, comprise an aromatic sulfonic acid group, and consist of sulfonated and crosslinked polystyrene granules.

The method for purifying phenol according to an exemplary embodiment of the present invention may obtain high-purity phenol by removing the high-boiling-point material converted from the hydroxyacetone, 2-methylbenzofuran and mesityl oxide by distilling the second fraction that has undergone the post-treatment process.

EXAMPLES

Hereinafter, examples of the present invention will be described in detail to be easily accomplished by those of ordinary skill in the art. However, the present invention may be implemented in a variety of different forms, and is not limited to the examples which will be described herein.

Examples 1 to 10: Method for Purifying Phenol

A feed was purified by the following method using a purification apparatus comprising a distillation column having a middle inlet to which the feed comprising phenol, acetone and hydroxyacetone was supplied, a first line connected to the upper part of the distillation column, a second line connected to the lower part of the distillation column, and a reflux pump connected with the distillation column and the first line.

Feeds shown in Tables 1 and 2 below were supplied to the distillation column through the middle inlet at temperatures shown in Tables 1 and 2 below, and subjected to distillation at operating pressures and temperatures shown in Tables 1 and 2 below.

The feed was separated such that the first fraction comprising the acetone was located in the upper part of the distillation column and the second fraction comprising the phenol was located in the lower part of the distillation column. Afterward, the second fraction comprising the phenol was recovered.

TABLE 1

| Classification | | Example 1 | Example 2 | Example 3 | Example 4 | Example 5 |
|---|---|---|---|---|---|---|
| Supply temperature (° C.) | | 60 | 70 | 80 | 95 | 95 |
| Feed composition (wt %) | Phenol | 47.0 | 47.0 | 47.0 | 47.0 | 45.0 |
| | Acetone | 30.0 | 30.0 | 30.0 | 30.0 | 28.0 |
| | Hydroxyacetone | 0.2 | 0.2 | 0.2 | 0.2 | 0.1 |
| | α-methyl styrene | 4.0 | 4.0 | 4.0 | 4.0 | 3.0 |
| | Low-boiling-point impurities | 6.4 | 6.4 | 6.4 | 6.4 | 13.1 |
| | High-boiling-point impurities | 1.4 | 1.4 | 1.4 | 1.4 | 0.8 |
| | Water | 11.0 | 11.0 | 11.0 | 11.0 | 10.0 |
| Operating pressure (kgf/cm² · g) | | 0.35 | 0.35 | 0.35 | 0.35 | 0.35 |
| Upper part temperature of column (° C.) | | 88 | 88 | 88 | 88 | 92 |
| Lower part temperature of column (° C.) | | 202 | 202 | 202 | 202 | 202 |

TABLE 2

| Classification | | Example 6 | Example 7 | Example 8 | Example 9 | Example 10 | Example 11 |
|---|---|---|---|---|---|---|---|
| Supply temperature (° C.) | | 95 | 95 | 95 | 95 | 95 | 95 |
| Feed composition (wt %) | Phenol | 47.0 | 47.0 | 48.0 | 47.0 | 49.0 | 46.0 |
| | Acetone | 30.0 | 30.0 | 30.0 | 30.0 | 31.0 | 29.0 |
| | Hydroxyacetone | 0.2 | 0.2 | 0.2 | 0.2 | 0.2 | 0.2 |
| | α-methyl styrene | 3.0 | 4.0 | 4.0 | 4.0 | 4.0 | 4.0 |
| | Low-boiling-point impurities | 8.1 | 6.4 | 6.1 | 6.4 | 6.1 | 6.1 |
| | High-boiling-point impurities | 1.7 | 1.4 | 2.7 | 1.4 | 1.7 | 2.7 |
| | Water | 10.0 | 11.0 | 9.0 | 11.0 | 8.0 | 12.0 |
| Operating pressure (kgf/cm² · g) | | 0.35 | 0 | 1 | 0.35 | 0.35 | 0.35 |
| Upper part temperature of column (° C.) | | 87 | 80 | 99 | 85 | 88 | 89 |
| Lower part temperature of column (° C.) | | 202 | 193 | 215 | 202 | 203 | 202 |

Low-boiling-point impurities: one or two or more of methanol, acetaldehyde, formaldehyde and cumene High-boiling-point impurities: one or two or more of cumylphenol, dicumyl peroxide, an α-methyl styrene dimer, and phenol tar Comparative Examples 1 to 4: Method for Purifying Phenol A feed was purified by a method which will be described below using a purification apparatus comprising a distillation column having a middle inlet to which the feed comprising phenol, acetone and hydroxyacetone was supplied, a first line connected to the upper part of the distillation column, a second line connected to the lower part of the distillation column, and a reflux pump connected with the distillation column and the first line.

A feed shown in Table 3 below was supplied to a distillation column through the middle inlet at a temperature shown in Table 3 below, and subjected to fractional distillation at operating pressures and temperatures shown in Table 3 below.

The feed was separated such that the first fraction comprising the acetone was located in the upper part of the distillation column and the second fraction comprising the phenol was located in the lower part of the distillation column. Afterward, the second fraction comprising the phenol was recovered.

TABLE 3

| Classification | | Comparative Example 1 | Comparative Example 2 | Comparative Example 3 | Comparative Example 4 |
|---|---|---|---|---|---|
| Supply temperature (° C.) | | 55 | 100 | 100 | 100 |
| Feed composition (wt %) | Phenol | 47.0 | 47.0 | 45.0 | 47.0 |
| | Acetone | 30.0 | 30.0 | 28.0 | 30.0 |
| | Hydroxyacetone | 0.2 | 0.2 | 0.1 | 0.2 |
| | α-methyl styrene | 4.0 | 4.0 | 3.0 | 3.0 |
| | Low-boiling-point impurities | 6.4 | 6.4 | 13.1 | 8.1 |
| | High-boiling-point impurities | 1.4 | 1.4 | 0.8 | 1.7 |
| | Water | 11.0 | 11.0 | 10.0 | 10 |
| Operating pressure (kgf/cm² · g) | | 0.35 | 0.35 | 0.35 | 0.35 |
| Upper part temperature of column (° C.) | | 88 | 88 | 92 | 87 |
| Lower part temperature of column (° C.) | | 202 | 202 | 202 | 203 |

Low-boiling-point impurities: one or two or more of methanol, acetaldehyde, formaldehyde and cumene High-boiling-point impurities: one or two or more of cumylphenol, dicumyl peroxide, an α-methyl styrene dimer, and phenol tar Experimental Example 1: Analysis of Components of Second Fraction Comprising Phenol Components of the second fractions of Examples 1 to 10 and Comparative Examples 1 to 4 were analyzed using gas chromatography, and the results are shown in Table 4 below.

TABLE 4

| Classification | Phenol (wt %) | α-methyl styrene (wt %) | Others (wt %) | Hydroxyacetone (wppm) |
|---|---|---|---|---|
| Example 1 | 92.2 | 2.1 | 5.6999 | 1 |
| Example 2 | 92.2 | 2.1 | 5.6998 | 2 |
| Example 3 | 92.2 | 2.1 | 5.6997 | 3 |
| Example 4 | 92.2 | 2.1 | 5.6977 | 23 |
| Example 5 | 95.9 | 0.9 | 3.1866 | 134 |
| Example 6 | 93.3 | 0.8 | 5.8962 | 38 |
| Example 7 | 92.3 | 2.0 | 5.6969 | 31 |
| Example 8 | 92.1 | 2.2 | 5.6986 | 14 |
| Example 9 | 92.7 | 1.5 | 5.7829 | 171 |
| Example 10 | 94.0 | 0.1 | 5.8174 | 826 |
| Example 11 | 91.4 | 3.0 | 5.5971 | 29 |
| Comparative Example 1 | 92.2 | 2.1 | 5.6999 | 1 |
| Comparative Example 2 | 92.2 | 2.0 | 5.7456 | 544 |
| Comparative Example 3 | 95.5 | 1.2 | 3.2042 | 958 |
| Comparative Example 4 | 93.2 | 0.8 | 5.9046 | 954 |

Referring to Table 4, concentrations of the hydroxyacetone in the second fractions of Examples 1 to 9 were in a range of 1 to 171 ppm, and it can be seen that, compared to the hydroxyacetone present in the feed supplied to the distillation column, the hydroxyacetone in the second fraction is considerably reduced.

In Example 10, since the feed was supplied at 95° C. but contained 8 wt % of water, a recovery amount of phenol was increased, but an effect of removing hydroxyacetone was not exhibited.

In Example 11, since the feed was supplied at 95° C. but contained 12 wt % of water, although an amount of hydroxyacetone was considerably reduced, an effect of separating α-methyl styrene was not exhibited, and phenol was lost compared to Examples 1 to 8.

From the results of Examples 10 and 11, it can be seen that since water was an azeotrope of phenol and α-methyl styrene, and hydroxyacetone was an azeotrope of phenol and α-methyl styrene, the efficiency of removing hydroxyacetone was increased by suitably maintaining the concentration of water, and the loss of phenol and α-methyl styrene was minimized.

Meanwhile, in Comparative Example 1, it can be seen that hydroxyacetone was reduced to the same level as Example 1. From the result, it can be seen that even when the feed supply temperature was lower than 60° C., the effect of reducing hydroxyacetone was not exhibited any more. However, due to the low feed temperature, energy consumed in a reboiler heating a distillation column was increased, compared to Example 1, and therefore, it can be inferred that energy efficiency was reduced.

In Comparative Examples 2 to 4, a content of hydroxyacetone in the second fraction was smaller than that in the feed supplied to the distillation column, but ten-fold or larger than those of Examples 1 to 8. Generally, when the temperature of the supplied feed was increased, energy consumed in the reboiler heating the distillation column was reduced, and therefore the feed temperature was increased to save energy. However, when the temperature of the supplied feed was higher than 95° C. as shown in Comparative Examples 2 to 4, the energy consumed in the reboiler was reduced, so that the hydroxyacetone moved to the lower part of the column was not sufficiently vaporized, and could not move to the upper part of the distillation column, and therefore it can be seen that the hydroxyacetone was not suitably removed.

Experimental Example 2: Analysis of Energy Efficiency of Distillation Column

Figure 2:
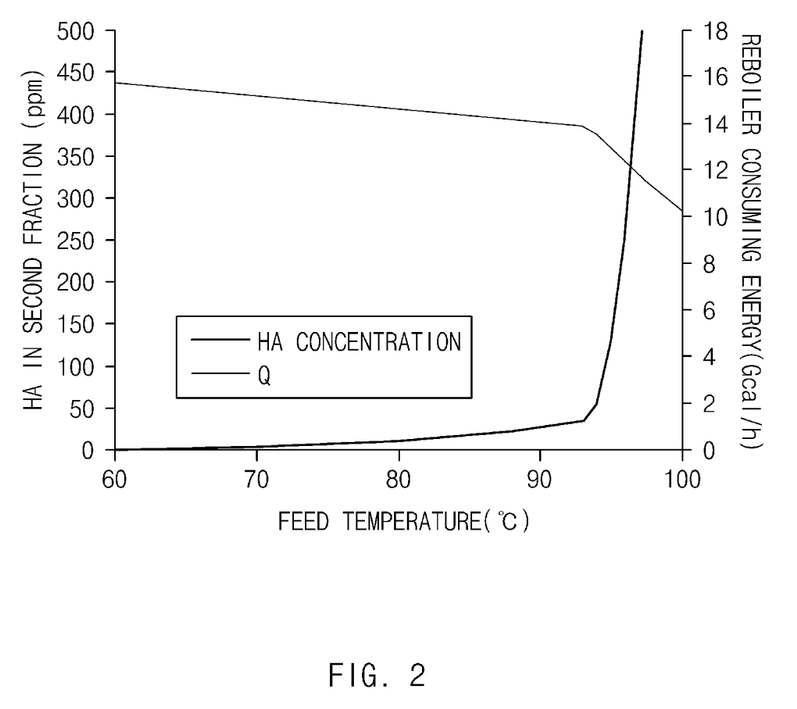
FIG. 2 shows the relationship between a content of hydroxyacetone in a second fraction of Examples 1 to 3 and Comparative Example 2, and energy consumed in a reboiler of a distillation column (reboiler duty).

The relationship between contents of the hydroxyacetone in the second fractions of Examples 1 to 3, and Comparative Example 2 and energy consumed in the reboilers of the distillation columns are shown in FIG. 2.

Meanwhile, on the X axis of FIG. 2, 60 indicates Example 1, 70 indicates Example 2, 80 indicates Example 3, and 100 indicates Comparative Example 2. The thick line indicates the content of hydroxyacetone in the second fraction, and the solid line indicates energy consumed in a reboiler of a distillation column.

Referring to FIG. 2, it can be confirmed that as the feed temperature increased, the energy consumed in the reboiler was reduced. In addition, it can be confirmed that when the feed temperature is higher than 95° C., the energy consumed in the reboiler was reduced, but the content of hydroxyacetone in the second fraction was rapidly increased. From the result, it can be confirmed that, considering both the efficiency of removing hydroxyacetone and energy efficiency, the suitable temperature range of the feed may be in a range of 80 to 95° C.

EXPLANATION OF REFERENCE NUMERALS

1: distillation column
10: middle inlet
11: first line
12: second line
21: reflux condenser
22: heat exchanger

The invention claimed is:

1. A method for purifying phenol, comprising:
supplying a feed comprising phenol, acetone, hydroxyacetone and water to a distillation column at 60 to 95° C.;
separating the feed into a first fraction which comprises the acetone and separates to the upper part of the distillation column and a second fraction which comprises the phenol and separates to the lower part of the distillation column; and
recovering the first fraction and the second fraction, respectively,
wherein the distillation column comprises a middle inlet to which the feed is input; a first line from which the first fraction is extracted; and a second line from which a second fraction is extracted,
wherein the distillation column does not comprise a middle outlet, and
wherein the feed comprises 40 to 70 wt % of the phenol, 15 to 45 wt % of the acetone, 0.02 to 5 wt % of the hydroxyacetone, and 9 to 11 wt % of water with respect to the total weight of the feed.

2. The method of claim 1, wherein the feed is prepared by oxidizing an alkylaryl compound to prepare a reaction mixture comprising an alkylaryl hydroperoxide and an unreacted alkylaryl compound and performing a cleavage reaction on the reaction mixture.

3. The method of claim 2, wherein the feed comprises one or more selected from the group consisting of cumene, α-methyl styrene, methanol, acetaldehyde, formaldehyde, cumylphenol, dicumyl peroxide, an α-methyl styrene dimer, mesityl oxide, 2-methylbenzofuran and phenol tar.

4. The method of claim 1, wherein the feed is supplied to the column at 75 to 95° C.

5. The method of claim 1, wherein the feed has a pH of 3 to 10.

6. The method of claim 1, wherein the hydroxyacetone in the second fraction is contained at 200 ppm or less based on weight of the second fraction.

* * * * *

UNITED STATES PATENT AND TRADEMARK OFFICE
CERTIFICATE OF CORRECTION

PATENT NO. : 10,532,968 B2  
APPLICATION NO. : 16/071553  
DATED : January 14, 2020  
INVENTOR(S) : Si Nae Lee et al.

Page 1 of 1

It is certified that error appears in the above-identified patent and that said Letters Patent is hereby corrected as shown below:

On the Title Page

Item (30), The Foreign Application Priority Data should read as follows:  
(30) Foreign Application Priority Data  
Nov. 14, 2016   (KR)    10-2016-0151394  
Nov. 9, 2017    (KR)    10-2017-0148530

Signed and Sealed this  
Seventh Day of July, 2020

Andrei Iancu  
*Director of the United States Patent and Trademark Office*